US008273117B2

(12) United States Patent
Palumbo et al.

(10) Patent No.: US 8,273,117 B2
(45) Date of Patent: Sep. 25, 2012

(54) LOW TEXTURE, QUASI-ISOTROPIC METALLIC STENT

(75) Inventors: Gino Palumbo, Toronto (CA); Peter Keng-Yu Lin, Toronto (CA); Klaus Tomantschger, Mississauga (CA); Fred Smith, Hannon (CA)

(73) Assignee: Integran Technologies Inc., Mississauga (CA)

( * ) Notice: Subject to any disclaimer, the term of this patent is extended or adjusted under 35 U.S.C. 154(b) by 979 days.

(21) Appl. No.: 11/157,833

(22) Filed: Jun. 22, 2005

(65) Prior Publication Data
US 2006/0292388 A1 Dec. 28, 2006

(51) Int. Cl.
*A61F 2/06* (2006.01)
(52) U.S. Cl. ...................................... 623/1.15; 428/586
(58) Field of Classification Search ................ 623/1.1, 623/1.11, 1.13, 1.15, 47; 29/17.2–17.9, 557, 29/558; 428/577, 548, 586; 148/516–536; 420/8, 16, 38, 452, 466, 468, 446; 72/253.1–273.5
See application file for complete search history.

(56) References Cited

U.S. PATENT DOCUMENTS

| | | | | |
|---|---|---|---|---|
| 4,733,665 A | | 3/1988 | Palmaz | 128/343 |
| 4,739,762 A | | 4/1988 | Palmaz | 128/343 |
| 4,990,197 A | * | 2/1991 | Das et al. | 148/307 |
| 5,195,984 A | | 3/1993 | Schatz | 606/195 |
| 5,262,104 A | * | 11/1993 | Schwartz | 264/81 |
| 5,421,955 A | | 6/1995 | Lau et al. | 216/48 |
| 5,611,670 A | * | 3/1997 | Yoshinari et al. | 416/241 R |
| 5,702,543 A | | 12/1997 | Palumbo | 148/592 |
| 5,817,193 A | * | 10/1998 | Palumbo | 148/325 |
| 5,836,964 A | * | 11/1998 | Richter et al. | 606/194 |
| 6,019,784 A | | 2/2000 | Hines | 623/1 |
| 6,107,004 A | | 8/2000 | Donadio, III | 430/320 |
| 6,129,795 A | * | 10/2000 | Lehockey et al. | 148/608 |
| 6,197,031 B1 | | 3/2001 | Barrette et al. | 606/80 |
| 6,599,316 B2 | | 7/2003 | Vardi et al. | 623/1.15 |
| 6,776,022 B2 | | 8/2004 | Kula et al. | 72/379.2 |
| 6,790,377 B1 | | 9/2004 | Cohen | 216/94 |
| 6,814,752 B1 | | 11/2004 | Chuter | 623/1.35 |
| 6,820,676 B2 | * | 11/2004 | Palmaz et al. | 164/46 |
| 7,344,560 B2 | * | 3/2008 | Gregorich et al. | 623/1.15 |
| 2002/0099436 A1 | * | 7/2002 | Thornton et al. | 623/1.12 |
| 2003/0082324 A1 | * | 5/2003 | Sogard et al. | 428/36.9 |
| 2004/0261919 A1 | * | 12/2004 | Nakajima et al. | 148/651 |
| 2005/0249776 A1 | * | 11/2005 | Chen et al. | 424/423 |
| 2006/0079954 A1 | * | 4/2006 | Burgermeister et al. | 623/1.15 |
| 2006/0100694 A1 | * | 5/2006 | Globerman | 623/1.35 |

FOREIGN PATENT DOCUMENTS
WO  WO 03/072287 A1  9/2003

OTHER PUBLICATIONS

King, B., et al., "Ceramic Laminates with the Fibrous Monolith", Architecture, paper presented Oct. 14, 1998 at Meeting of the Minerals, Metals & Materials Society in Chic., II, p. 96-97 of program.

* cited by examiner

*Primary Examiner* — Victor Nguyen
(74) *Attorney, Agent, or Firm* — Bacon & Thomas, PLLC

(57) ABSTRACT

Metallic stents which have a randomly oriented microstructure, and possess quasi-isotropic mechanical and physical properties are disclosed. The novel stents can be "tailor-made" to mimic the geometry of the blood vessel(s) at the deployment site and can be designed to treat coronary artery disease at the point where blood vessels branch. The metallic materials of choice are ductile, corrosion resistant and exhibit little crystallographic texture. The novel stents can be produced from a metallic precursor which is quasi-isotropic and exhibits little texture by processing means, such as machining, which do not reintroduce texture. Alternatively, quasi-isotropic and low texture stents are achieved by suitable post-processing of conventionally fabricated stent materials.

2 Claims, 1 Drawing Sheet

LOW TEXTURE, QUASI-ISOTROPIC METALLIC STENT

TECHNICAL FIELD

This invention relates to the manufacturing of stents having quasi-isotropic physical and mechanical properties and a randomly oriented microstructure. This invention allows for the precision machining of stents from bar, rod and plate feedstock materials which have little or negligible crystallographic texture.

BACKGROUND OF THE INVENTION

The development of balloon-expandable coronary stents marked a significant advance in the treatment of coronary artery disease by providing an alternative to balloon angioplasty and bypass surgery. Stents are thin walled tubular-shaped devices which hold open a segment of a blood vessel. Stents are typically implanted in the "radially collapsed state" by a catheter which is inserted at an easily accessible location and then advanced through the vasculature to the deployment site. Once in position, the stent is deployed by inflation of a dilation balloon.

The stent must have the following properties:
1. adequate radial strength (hoop strength), capable of withstanding the structural loads exerted on the stent as it supports the walls of a vessel lumen;
2. longitudinal flexibility to allow it to be maneuvered through a tortuous vascular path;
3. sufficient ductility to provide the required flexibility during insertion and sizing at the deployment site;
4. conformity to the deployment site "geometry" that may not be round or straight and may be subject to flexure;
5. ability to be placed at or near branch points of vessels;
6. ability of the material to undergo sizing (compression and/or expansion) which requires substantial deformation of at least part of the stent's structure;
7. size retention, once expanded, throughout its service life and ability to keep withstanding the various forces including the cyclic loading induced by the beating heart;
8. biocompatibility;
9. ability to be sufficiently radiopaque or fluoroscopically visible under x-ray to allow accurate stent placement using real-time visualization enabling tracking the delivery catheter through the patient's vasculature and precise placement of the stent at the site of a lesion.
10. convenient and economic to manufacture with high production yield.
11. high reliability in use and adequate longevity.

Stents are typically made of stainless steel, cobalt alloys or nickel-titanium alloys, all of which, at the relatively thin wall thickness of about 50 to 150 micron, are sufficiently radiopaque to be visualized with x-ray based fluoroscopy procedures.

It is well known in the art that shaping and forming of metals (i.e., sheets, rods, tubes) using deformation steps in the processing results in the alignment of grains along certain preferred crystallographic orientations. Invariably all metal working processes introduce some directionality (i.e., texture) to the crystal structure and as a result, the anisotropic properties of single crystals of a metal are imparted to the polycrystalline aggregate in various degrees. Both elastic and plastic mechanical properties are dependent on crystallographic orientation.

The fundamental basis for understanding the deformation behavior of a crystalline solid and its dependence on crystal orientation is known as the Schmid law. According to this law, the plastic flow is carried by slip on a crystallographic slip system which is a certain combination of a crystallographic plane and a crystallographic direction in this plane. The deformation process in single crystals was studied extensively and the anisotropy of elastic modulus in single crystals has been summarized by Schmid and Boas (Schmid and Boas, Plasticity of Crystals, Hughes, London, 1950, p. 191). The degree of anisotropy varies considerably even from metal to metal of the same crystallographic system.

Depending on the nature of the crystallographic texture and the intended use of the material, anisotropy may or may not be a desirable feature from the practical viewpoint. It is often necessary to design a specific crystallographic texture for a particular purpose. A sharp texture in non-ferrous metal and alloys is generally considered to be undesirable because of the occurrence of earing and fracture during the fabrication process. In the fabricated metal products a completely random orientation is generally considered to be exceptional and highly desirable. This is also preferred for applications requiring a high degree of reliability such as coronary stents.

Stent tubes are typically made from drawn tubes or from rolled sheets. It is well documented that in f.c.c. (face-centered cubic) metals the deformation texture associated with tube forming is usually composed of [111] and [100] components (Hsun, Hu, Texture of Metals, Texture, vol. 1, p. 233-258, 1974). Even after annealing, the [111] and [100] duplex fiber texture is usually retained with some scattering. During placement of the metallic stents, the stent can undergo significant plastic deformation (i.e., from crimping and expansion procedures) in order to achieve the required diameter. The plastic deformation is known to create residual stresses. The dilation of the stents leads to a concentration of tensile and compressive residual stresses in different areas of the nodes of the stent. Since the stent is comprised of a network of small wire segments with a cross section of 50-150 microns in thickness and a nominal grain size of 25 to 30 microns, each stent wire essentially contains only a few grains in the thin cross-section. The accumulation of the residual stresses in such a thin section can therefore be influenced by the local grain crystallographic orientations and cause a weakening of the mechanical stability of the stent structure and reduce the reliability of the device during insertion and in service. The thin, multi-directional stent wires ideally require isotropic properties in all directions, a randomly oriented microstructure and a low texture intensity value to optimize the uniformity of deformation during emplacement and to maximize performance and reliability. Specifically, the reduction in the local texture variances has practical importance in minimizing the anisotropy arising from both the residual stresses during device implantation and the load stresses from cyclic heart beats while the device is in service. The specific benefits this invention provides therefore relate to the improvement in material performance (i.e., resistance to fatigue crack) and device longevity (i.e., stress corrosion cracking and dissection of the artery wall by a broken stent strut).

The patent literature on various features of stent designs is extensive. Generally stents are formed by e.g. laser cutting a tube to imprint a suitable pattern. Stent tubes are typically produced by drawing to form a thin metal tube of the appropriate dimensions, or by folding and welding a thin sheet. Other fabrication methods include direct forming e.g. using electroforming or sputtering.

Various patents disclose stents made from anisotropic and textured drawn tubes including thin walled and slotted structures produced from drawn tubes exhibiting a significant texture and anisotropic properties and include:

J. Palmaz in U.S. Pat. No. 4,739,762 (1988) discloses an expandable and deformable intraluminal vascular graft which is expanded within a blood vessel by an angioplasty balloon associated with a catheter to dilate and expand the lumen of a blood vessel. The graft may be a thin-walled tubular member having a plurality of slots disposed substantially parallel to the longitudinal axis of the tubular member.

R. Schatz in U.S. Pat. No. 5,195,984 (1993) discloses a plurality of expandable and deformable intraluminal vascular grafts which are expanded within a blood vessel by an angioplasty balloon associated with a catheter to dilate and expand the lumen of a blood vessel. The grafts may be thin-walled tubular members having a plurality of slots disposed substantially parallel to the longitudinal axis of the tubular members. Adjacent grafts are flexibly connected by a single connector member disposed substantially parallel to the longitudinal axis of the tubular members.

J. V. Donadio in U.S. Pat. No. 6,107,004 (2000) describes a manufacturing process for slotted tubes for use as catheters. The manufacturing process includes creating a pattern of slots or apertures in a flexible metallic tubular member by processes including electrostatic discharge machining (EDM), chemical milling, ablation and laser cutting. These slots or apertures may be cut completely or partially through the wall of the flexible metallic tubular member. These manufacturing processes may also include the additional step of encasing the flexible metallic member such that a fluid-tight seal is formed around the periphery of the tubular member.

Patents addressing forming stents from thin sheets exhibiting anisotropic properties and texture include:

J. Kula in U.S. Pat. No. 6,776,022 (2004) describes a flexible stent made from a metal sheet. The sheet is rolled in its central region to a specified wall thickness. Thereafter, the stent is photochemically etched to produce the desired cell pattern of the design of the stent. Then, the stent is folded and the metal is joined to give rise to a stent with multiple wall thickness. Typically, the ends of the stent comprise larger wall thicknesses whereas the wall thickness at its center remains smaller.

Various patents address cutting stents from anisotropic and textured tube-feedstock and include:

M. Reed in WO03072287A1 (2003) describes a methods for fabricating implantable medical devices having microstructures on tubular or cylindrical surfaces. A precursor tube fabricated from stainless steel, titanium, nitinol or tantalum, having an outer surface coated with a photoresist material, is treated to define an optical pattern on the photoresist material and the outer surface is etched electrochemically to form the desired microstructure. Thereafter, the photoresist material is removed and the device precursor is machined to form the implantable tubular medical device.

L. Lau in U.S. Pat. No. 5,421,955 (1995) describes an expandable stent for implantation in a body lumen, such as an artery, and a method for making it from a single length of tubing. The stent consists of a plurality of radially expandable cylindrical elements generally aligned on a common axis and interconnected by one or more interconnective elements. The individual radially expandable cylindrical elements consist of ribbon-like materials disposed in an undulating pattern. The stents are made by coating a length of tubing with an etchant-resistive material and then selectively removing portions of the coating to form a pattern for the stent on the tubing and to expose the portions of the tubing to be removed. This may be done by machine-controlled activation and relative positioning of a laser in conjunction with the coated tubing. After the patterning of the tubing, the stent is formed by removing exposed portions of the tubing by an etching process.

Patents addressing alternative methods for forming stents include:

Electroforming of stents is disclosed in R. A. Hines in U.S. Pat. No. 6,019,784 (2000). The process for making electroformed stents involves coating a mandrel with a resist, exposing portions of the resist to light to form a stent pattern, metal plating the mandrel and then dissolving the mandrel. As electroforming is a linear deposition process, the resulting stent would be expected to possess some degree of fiber texture and development of columnar grains in the radial direction.

A. Cohen in U.S. Pat. No. 6,790,377 (2004) describes an electroplating method to form a layer by i) contacting a substrate with a first article which includes a support and a conformable mask; ii) electroplating a first metal from a source of metal ions onto the substrate in a first pattern, the first pattern corresponding to the complement of the conformable mask pattern; and iii) removing the first article from the substrate. The method may further involve selectively or non-selectively depositing one or more additional materials to complete the formation of the layer, planarizing the deposited material after one or after each deposition step and/or forming layers adjacent to previously formed layers to build up a structure from a plurality of adhered layers. As electroplating is also a linear deposition process, the various adhered layers described in this patent would also be expected to possess some degree of fiber texture in the radial direction.

J. Palmaz in U.S. Pat. No. 6,820,676 (2004) describes implantable endoluminal devices which are fabricated from materials which provide a blood or body fluid and tissue contact surface and exhibits controlled heterogeneities in the material constitution. The stents are fabricated using vacuum deposition methods. As vacuum deposition is also a linear deposition process, the implant described in this patent would also be expected to possess some degree of fiber texture and development of columnar grains in the radial direction.

Until recently, conventional stents were produced in a straight tubular configuration. The use of such stents to treat vessels at or near a branch point is not without risk. Ideally, stents are tailor made to the specific location of placement, can be placed in locations where vessels branch, can be used to treat lesions in the "main" as well as the "side" branch of a vessel allowing for different stent shapes and sizes to be implanted.

Various patents address stents with a main tubular stent body having one or more side openings which may further comprise an extendable or second stent inserted through the side opening and at least partly in registry with the wall of the side opening.

G. Vardi in U.S. Pat. No. 6,599,316 (2003) describes stents for use in treating lesions at or near the bifurcation point in bifurcated cardiac, coronary, renal, peripheral vascular, gastrointestinal, pulmonary, urinary and neurovascular vessels and brain vessels. The invention discloses a stent apparatus with at least one side opening which may further comprise an extendable stent portion laterally extending from the side opening and at least partly in registry with the wall of the side opening. Devices constructed in accordance with the invention include a main expandable stent comprising at least one substantially circular side opening located between its proximal and distal end openings, where the side opening may further comprise an expandable portion extending radially outward from the edges of the side opening; and a branch stent comprising proximal and distal end openings which may further comprise a contacting portion at its proximal end, and which may optionally be constructed to form either a perpendicular branch or a non-perpendicular branch when inserted through a side opening of the main stent.

T. Chuter in U.S. Pat. No. 6,814,752 (2004) describes a system and method for treating and repairing complex anatomy characterized by a plurality of vessel portions oriented at various angles relative to each other. The system includes a graft device that is capable of being assembled in situ and has associated therewith a method that avoids the cessation of blood flow to vital organs. A delivery catheter system and various graft supporting, mating and anchoring structures are also included.

The novel stents proposed herein have essentially isotropic properties in all directions, exhibit little crystallographic texture and can be "tailor-made" to mimic the geometry of the blood vessel(s) at the deployment sites. The stents can be machined from metallic material feedstock which is ductile, corrosion resistant and has a quasi-isotropic, randomly oriented microstructure with no specific texture. Furthermore the stents can be designed to treat coronary artery disease at the point where blood vessels branch.

SUMMARY OF THE INVENTION

It is an objective of the invention to provide stents using metals and metal alloys which are ductile, corrosion resistant and radiopaque exhibiting quasi-isotropic properties, a randomly oriented microstructure and a low texture intensity value.

It is an objective of the invention to provide stents which contain a quasi-isotropic, randomly oriented microstructure exhibiting fairly uniform mechanical properties in all directions. Quasi-isotropic in this context refers to a microstructure that exhibits little crystallographic texture and possesses grains that are reasonably uniform in shape and size in all directions, and possesses mechanical properties, which are similar throughout the material.

It is an objective of the invention to provide stents having a low texture intensity value. In texture analysis the intensity of the texture is expressed in terms of a multiple of that expected in a completely random distribution. A value of 1 indicates a totally randomized crystallographic texture. Texture intensity values higher than 1 are indicative of some crystallographic texture, the higher the value the stronger the texture.

It is an objective of the invention to provide stents which do not necessarily have a circular cross-section but also include oval and/or irregular cross sections and are not necessarily straight in the longitudinal direction but may be shaped irregularly as is the case for typical blood vessels.

It is an objective of the invention to utilize a process capable of "tailor-making" stents to mimic the geometry of blood vessels at the deployment site.

It is an objective of the invention to enable the use of a predetermined article surface finish/texture/roughness which e.g. on the outer surface can be somewhat rough to enhance the anchoring at the deployment site while on the inner surface is typically very smooth to enhance laminar blood flow through the stent.

It is an objective of the invention to provide stents which can be used to treat coronary artery disease at the point where blood vessels branch.

It is an objective of the invention to apply conventional and advanced machining processes including EDM, CNC milling, laser cutting, water jetting, honing, electrochemical machining and chemical machining to form the stents from "bulk feed-stock".

It is an objective of the invention to utilize fabrication methods which are highly reproducible and capable of producing small parts. The methods enable the production of stent devices that are typically too large for conventional microfabrication techniques and too small for traditional precision machining techniques.

It is an added objective of the invention to provide stents exhibiting a recrystallized microstructure.

It is an objective of the invention to provide metal stent materials of high ductility.

It is an added objective of the invention to provide stents which have been processed using grain boundary engineering.

It is an added objective of the invention to provide stents which have a special grain boundary fraction (Fsp) of at least 50%.

It is an objective of the invention to enhance the long term biocompatibility of metal stent materials and to enhance their corrosion resistance; reducing leaching of metals causing health concerns e.g. nickel in the case of stainless steels and optionally encase the metallic stent in a biologically inert material.

Accordingly, the invention provides stents which can be manufactured by a process for machining isotropic round, oval or irregularly shaped and branched tubular members from bulk metal blocks. Bulk metal blocks in this context are defined as metal sheets, rods etc. not exhibiting a noticeable directional dependence of mechanical properties which have not been formed by a deformation process (drawing, rolling etc.), or if a deformation process was employed, have been subsequently recrystallized by a suitable heat treatment to establish a quasi-isotropic, randomly oriented microstructure. The stent precursor is cut from the metal feedstock and suitably hollowed out. Openings are cut into the sidewalls of the stent precursor tube to introduce slots or other desired patterns to form the expandable metallic stent.

According to one aspect of the present invention, the isotropic starting material for the stent is obtained e.g. by casting a block, rod or the like of the desired chemical composition.

According to another aspect of the present invention the starting material is highly textured e.g. as rolled sheet, extruded rod, drawn tube or the like and is suitably rendered isotropic e.g. by a suitable heat-treatment e.g. a recrystallization heat treatment before it is used as a stent.

BRIEF DESCRIPTION OF THE DRAWINGS

In order to better illustrate the invention by way of examples, descriptions are provided for suitable embodiments of the method/process/apparatus according to the invention in which.

PREFERRED EMBODIMENTS OF THE INVENTION

This invention relies on producing stents having quasi-isotropic physical and mechanical properties. This invention further relies on the precision machining of stents from wrought bar, rod and plate materials which preferably have a quasi-isotropic, randomly oriented microstructure with little crystallographic texture. Suitable machining processes are selected from the group of EDM, CNC milling, laser cutting, water jetting, honing, electrochemical machining and chemical machining.

Figure 1:
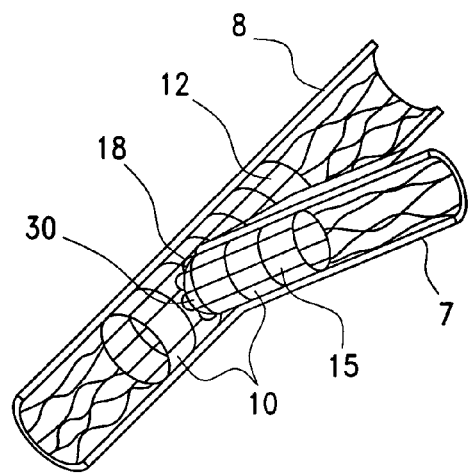
FIG. 1 is a schematic depiction of a branched stent.

FIG. 1 illustrated a branched-stent 10 comprising a suitable perforated, cylindrical main stent-tube 12 and a suitably perforated, cylindrical branch stent-tube 15 shown as fully dilated in a main blood vessel 8 and the branched vessel 7. The main stent-tube 12 contains at least one generally round side opening 18 located between the two ends of the main stent-tube 12. As indicated the stent tubes 12 and 15 are perforated and the remaining solid elements/wires/expandable struts 30 are schematically illustrated.

Stents are tubes designed to be inserted into a vessel or passageway in the human body to keep it open and maintain suitable fluid flow. They are used in narrowed sections of coronary and carotid arteries. Stents are also used in other structures such as the esophagus to treat a constriction, ureters to maintain the drainage of urine from the kidneys, and bile ducts.

In the case a branched stent as depicted in FIG. 1 is applied, the branched-stent tube 15 is suitably collapsed and folded into the main stent-tube 12 to the degree necessary to enable the insertion of branched stent by a catheter which is inserted at an easily accessible location and then advanced through the vasculature to the deployment site. Alternatively, the main stent and the branched stent are deployed separately and joined at the deployment site. If the stent is "tailor made" to fit the geometry of the deployment site, the deployment location is suitably visualized and the shape, size, cross-section etc. of the vessel to be stented is determined and, taking into consideration the degree of blockage the appropriate size, shape and cross-section of the expanded stent accordingly determined.

The following listing describes suitable parameter ranges for practicing the invention:

Overall stent size (maximum length) [cm]: 0.1-10.0
Expanded stent outside diameter (OD) equivalent (maximum diameter) [mm]: 0.5 to 10.0
Stent wall thickness [mm]: 0.025 to 1.5
Overall stent volume [cm$^3$]: 0.1 to 25
Overall stent precursor weight [g]: 0.1 to 25
Minimum Ductility [%]: 5, 10
Maximum Ductility [%]: 50, 75
Minimum $F_{sp}$ [%]: 50, 55, 60
Maximum $F_{sp}$ [%]: 75, 85, 95
Minimum texture intensity [times random value]: 1, 2
Maximum texture intensity [times random value]: 5, 6

Stents currently employed typically use drawn minitube precursors which are laser cut to the desired geometry. The shape of the pattern dictates the expansion properties of the finished stent. The use of laser micromachining enables stent designs that are more maneuverable in the tortuous coronary anatomy, yet remain strong enough to provide adequate scaffolding for diseased vessels. Laser cutting leaves an oxide layer on the surface of the stent which is cleaned off subsequently e.g. by electro-polishing.

Numerous vendors provide stent precursors focusing mainly on 316L, Nitinol and Co—Cr—Mo tubing. As is known to persons skilled in the art, products produced by a forming operation, such as drawing and rolling, are highly textured and exhibit anisotropic properties.

Machining stents from a quasi-isotropic metal block exhibiting little or no texture enables the elimination of the directional dependence of mechanical properties.

Suitable biologically-inert metallic materials for use in stents include metals selected from the group of shape-memory alloys, stainless steels, and/or alloys of titanium, tantalum, vanadium, cobalt, chromium, molybdenum and platinum. The stent material must be biocompatible so that it is neither absorbed nor rejected by the body. Body fluids are known to be highly corrosive to many metals; therefore the metallic material must be corrosion resistant to blood and other body fluids. It is common practice to encase the metallic stents with a biologically inert material which forms a fluid-tight coating, e.g., a gold coating or a polymeric (e.g., Parylene) coating and/or to include a drug delivery coating.

Ideal stent precursors exhibit isotropic properties, are not limited by the design constraints of tubes and are conveniently, and economically "tailor-made" to mimic the exact geometry of the vessels at the deployment site. Moving away from tube precursors enables the use of circular, oval and/or even totally irregular cross sections and the fabrication of stent precursors that are not necessarily straight in the longitudinal direction but shaped irregularly as is the case for typical blood vessels. It is desirable for stent precursors to provide the ability to use a variable wall thickness. Increasingly stents are required which can be used to treat coronary artery disease at the point where blood vessels branch. Branches of vessels typically involve variable sizes, variable orientations and variable positions and need be stented with "custom made" stents to overcome all limitations highlighted before.

Frequently it is desirable to "tailor-make" the stents to mimic the desired geometry of blood vessels at the deployment site. Although lumens generally have a circular cross-section, oval and/or irregular cross sections and cross-sections which vary in dimensions along the length of the lumen are not uncommon. They are also not necessarily straight in the longitudinal direction but shaped irregularly as is the case for typical blood vessels. It is understood that the stent will not match the current exact geometry of the vessel at the deployment site, as its purpose is to counteract clogging/narrowing of the vessel and expand/restore the vessel to its original size and shape. Based on the actual geometry of the vessel at the deployment site a suitable geometry for the stent is chosen which once placed and expanded at the site, will exert the desired radial expansion force to the lumen passage way which is deemed appropriate. If the stent is "oversized" it can potentially cause rupturing of the passageway of the blood vessel. "Undersized" stents potentially insufficiently expand the passageway effectively or even fail to secure sufficient contact to the blood vessel at the deployment site rendering the stenting ineffective and potentially causing migration of the stent with time. In addition, the dimensions of the stent precursor also take into account that the outer dimensions change during post processing which typically include laser cutting, chemical and/or electrochemical etching and polishing as well as applying polymer and drug containing coatings to the metal stent.

The person skilled in the art of grain boundary engineering (GBE) will know how to process feedstock material specifically suitable for this application. GBE processed materials, in addition to being isotropic, also provide enhanced ductility and superior corrosion performance when compared to as-cast or deformed counterparts. For reference, suitable materials made of face centered cubic alloys including austenitic stainless steels are disclosed in U.S. Pat. No. 5,817,193 (1998) wherein the alloy is cold worked and subsequently annealed and these deformation/annealing cycles are optionally repeated to achieve a fully recrystallized microstructure. The resulting product has a grain size not exceeding 30 microns, a "special" grain boundary fraction as defined in U.S. Pat. No. 5,817,193 of not less than 60%, and major crystallographic texture intensities all being less than twice that of random values. The product has a greatly enhanced resistance to intergranular degradation and stress corrosion cracking, and possesses highly isotropic bulk properties. Suitable processing methods to establish desired feedstock materials are also disclosed in U.S. Pat. No. 5,702,543 (1997) and U.S. Pat. No. 6,129,795 (2000).

Working Example

As outlined, it is well known that metal tubes and wires produced by drawing develop a preferred orientation, typically a uniaxial or fibrous texture. In a fibrous texture most of the grains are aligned parallel to the longitudinal axis. Specific crystallographic directions are oriented parallel to the tube/rod axis and frequently another preferred orientation develops in the radial direction (cyclic texture). Furthermore there are usually differences in orientation and texture at the surface and the interior. Specifically to tubes, the crystallographic texture developed depends on the relative reductions of wall thickness and tube diameter. When the wall thickness and diameter of a tube are reduced proportionally, the texture is similar to that of a rod or wire. If only the wall thickness is reduced the texture resembles the one of a rolled sheet. When only the tube diameter is reduced without affecting the wall thickness preferred orientations develop in directions tangential to the circumference.

Texture analysis is a statistical methodology for analyzing the distribution of crystallographic orientation in polycrystalline materials. Texture analysis is commonly represented by pole figures which are stereographic projections with a specific orientation relative to the specimen that show the variation in pole orientation for selected sets of crystal planes and texture intensity values. The intensity of the texture is usually expressed in terms of times random. The higher the number is indicative of the stronger texture. The texture and special grain boundary information was obtained using TSL's orientation imaging microscopy (OIM) system (EDAX, Mahwah, N.J., U.S.A.), an automated electron backscatter diffraction (EBSD) and crystallographic analysis system attached to a JSM 840A SEM (JEOL Ltd, Tokyo, Japan) scanning electron microscope.

As discussed, differences in orientation result in varying mechanical properties displaying a directional dependence which is undesirable. 316LVM stainless steel stent precursor tubes and bar and plate feedstock were sourced or fabricated according to the process of the invention and thereafter characterized. All stent precursor tubes sourced or fabricated had similar dimensions (~1" long, 0.020"ID and 1/16"OD). Conventional, prior art, drawn tubes (AR316) were sourced from Western Analytical (Western Analytical Products, Lake Elsinore, Calif., U.S.A). A set of tubes was machined by electrical discharge machining (EDM) from 316LVM commercial sheet feedstock. A third set of tubes was machined the same way but from rolled and heat-treated (grain boundary engineered) 316LVM feedstock. Grain boundary engineering was performed as taught in U.S. Pat. No. 5,702,543 (1997) and U.S. Pat. No. 6,129,795 (2000) by applying three consecutive deformation/heat treatment cycles involving a 10%-70% rolling reduction, followed by a heat treatment at 1030° C. for 2 minutes in an argon gas atmosphere. The attached table highlights the comparative data.

TABLE 1

|  | (a) Prior art/ drawn tube | (b) Machined tube/this invention | (c) Machined GBE'd tube/this invention |
| --- | --- | --- | --- |
| Production process | Drawn tube (AR316) | Machined tube from commercial 316LVM sheet | Machined from grain boundary engineered 316LVM sheet |
| Length [cm] | 2.5 | 2.5 | 2.5 |
| OD [mm] | 0.625 | 0.625 | 0.625 |
| Wall thickness [mm] | 0.11 | 0.11 | 0.11 |
| Grain size [μm] | 30 | 30 | 30 |
| Texture Intensity Value | 6.8 | 5.0 | 2.5 |
| Special grain boundary fraction Fsp [%] | 50-55 | 55 | 70 |
| Yield Strength [ksi] | 27.5-100 | 37.9 | 36.6 |
| UTS [ksi] | 71-125 | 90.8 | 86.7 |
| Elongation [%] | 10-40 | 20 | 50 |

The comparative data highlight the significant differences in texture between prior art/drawn tube stent precursor tubes and the present invention (machined GBE processed tube). The substantial increase in Fsp for grain boundary engineered feedstock results in superior corrosion performance and ductility. The data also shows a range for each of yield strength, UTS and elongation present for prior art drawn tubes demonstrating anisotropy (directional dependence) for the prior art, and fixed values for (b) and (c) illustrating quasi-isotropy for the invention herein.

Figures 2A, 2B:
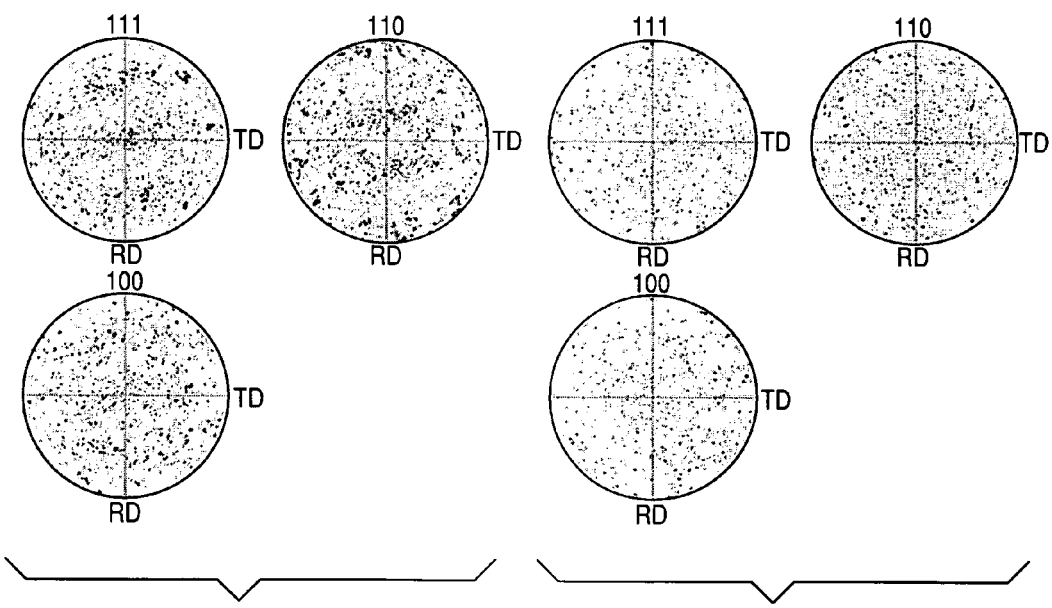
FIG. 2 highlights the significant differences in texture between prior art stent precursor tubes and the present invention.

FIG. 2 shows discrete Pole Figures showing the difference in the texture characteristics between (a) prior art or commonly drawn tube (i.e., <111>+<100> fiber texture) (FIG. 2(a)) and (b) machined from GBE processed sheet (i.e., randomized texture) (FIG. 2(b)).

Similar results were obtained when the metallic material used was Nitinol and Co-bearing alloys and when branched stent precursors were produced. While several specific embodiments of the invention have been illustrated and described, it will be apparent that various modifications can be made without departing from the spirit and scope of the invention. Accordingly, it is not intended that the invention be limited, except as by the appended claims.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A method for manufacturing a metallic precursor tube, for a biocompatible, expandable, flexible intraluminal graft, comprising the steps of
    (a) providing a bulk metal block which is quasi-isotropic in all directions, which has not been formed by a deformation process, or if formed by a deformation process, has been subsequently recrystallized by heat treatment, to establish a quasi-isotropic, randomly oriented microstructure,
    (b) machining said quasi-isotropic bulk metal block by cutting and hollowing out to provide a precursor tube having a first and second end and having a size and shape selected to reflect a geometry of a vessel or vessels at a deployment site and comprising a thin walled member with a wall thickness ranging from 0.025 to 1.5 mm and having an outside diameter ranging from 0.5 to 10.0 mm and exhibiting a quasi-isotropic, randomly oriented microstructure, and a texture intensity value in the range of 2.5 to 6 times random.

2. The method according to claim 1 where openings are cut into the wall of said metallic precursor tube to form an expandable metallic stent.

* * * * *